(12) United States Patent
Heilmann et al.

(10) Patent No.: US 7,713,412 B2
(45) Date of Patent: *May 11, 2010

(54) FILTER DEVICE

(75) Inventors: Klaus Heilmann, St. Wendel (DE); Gerhard Breith, Pirmasens (DE); Igor Raiko, St. Wendel (DE); Roland Sander, St. Wendel (DE); Steffen Fritzsche, Tholey (DE)

(73) Assignee: Fresenius Medical Care Deutschland GmnH, Bad Homburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/118,336

(22) Filed: May 9, 2008

(65) Prior Publication Data

US 2008/0230467 A1   Sep. 25, 2008

Related U.S. Application Data

(63) Continuation of application No. 10/675,310, filed on Sep. 29, 2003, now abandoned, which is a continuation of application No. 09/464,605, filed on Dec. 15, 1999, now Pat. No. 6,641,731.

(30) Foreign Application Priority Data

Dec. 15, 1998  (DE) ................................ 198 57 850

(51) Int. Cl.
*B01D 63/02*  (2006.01)
*B01D 61/24*  (2006.01)
*B01D 61/00*  (2006.01)

(52) U.S. Cl. ........................... 210/321.79; 210/321.88; 210/321.71; 210/456; 422/44; 422/45

(58) Field of Classification Search ....................... None
See application file for complete search history.

(56) References Cited

U.S. PATENT DOCUMENTS

| 4,141,835 A | * | 2/1979 | Schael et al. ........... 210/321.81 |
| 5,578,267 A | * | 11/1996 | Cosentino et al. ............. 422/46 |
| 6,053,967 A | * | 4/2000 | Heilmann et al. ............. 96/208 |
| 6,426,002 B1 | * | 7/2002 | Hahmann et al. ...... 210/321.79 |
| 6,641,731 B1 | * | 11/2003 | Heilmann et al. ...... 210/321.79 |

FOREIGN PATENT DOCUMENTS

| DE | 3435883 A | * | 4/1986 |
| EP | 0 646 380 | | 8/1994 |

* cited by examiner

*Primary Examiner*—Krishnan S Menon
(74) *Attorney, Agent, or Firm*—Kenyon & Kenyon LLP

(57) ABSTRACT

A hollow fiber filter device for dialysis having a housing and an end cap is described. The end cap is attached to an axial end of the housing, and has a curved channel in fluid communication with a fluid port, a fluid chamber having a flow path defined by a plurality of curved members connected to an upper interior surface. The distance between circumferentially adjacent curved members may decrease in a radially outward flow direction.

49 Claims, 6 Drawing Sheets

FILTER DEVICE

CROSS-REFERENCE TO RELATED APPLICATIONS

This application is a continuation of prior application U.S. Ser. No. 10/675,310, filed Sep. 29, 2003, now abandoned, which is a continuation application of prior application U.S. Ser. No. 09/464,605, filed Dec. 15, 1999, now U.S. Pat. No. 6,641,731, each of which is expressly incorporated herein in its entirety by reference thereto.

FIELD OF THE INVENTION

The present invention concerns a filter device for mass exchange between two media separated by a membrane and an end cap for such a filter device.

BACKGROUND OF THE INVENTION such filter devices are generally used as dialyzers, hemofilters or ultrafilters. The filter devices generally consist of a casing in the form of a tubular section with end caps in its end areas. A tubular fiber bundle which functions as a membrane is usually arranged in the casing so that a reliable seal is provided between the first flow space formed by the fiber cavities and a second flow space surrounding the membrane on the outside.

One problem with the design of the inflow and/or outflow chambers connected to the first flow space, i.e., to the hollow fiber bundle, is how to distribute the liquid so that it is apportioned evenly to the individual fibers of the hollow fiber bundle, and so that dead zones in the distribution of liquid are avoided.

There are known dialyzers where the inlet of the chambers connected to the hollow fiber bundle is arranged axially, with the axis of the flow channel running approximately through the mid point of the hollow fiber bundle. This generally yields the disadvantage that use of the fibers varies greatly, and at the same time there are areas where the flow velocity is approximately zero (dead zones). After finishing a dialysis treatment, such dead zones are the areas where the patient's blood remains behind. In addition, there is a great difference between the flow velocity in the inlet and that in the fibers. The blood is exposed to a stress situation due to the resulting velocity gradient.

Unexamined German Patent DE-OS 26 46 358 describes a filter device where the end caps have a tangential inlet and the blood is carried in a channel in circulation through the ends of the hollow fibers. Blood flows tangentially through the hollow fiber ends. To achieve the most uniform possible distribution of liquid, only the areas of the casting compound in overflow circulation are provided with hollow fibers, while the rest of the core area does not have any fibers. This achieves uniform loading of the fibers but also results in a relatively low capacity or suboptimal utilization of the filter device on the whole due to the lack of hollow fibers at the center of the casing. To achieve a uniform rate of circulation of blood in the channel, the cross-sectional area of the channel in one embodiment decreases in the direction of flow.

It has also been proposed that the inlet be located parallel to the plane of the fiber ends and that the medium should change directions by 90 degrees in the end area of the inlet. Due to the small amount of available space and the manufacturing restrictions due to the injection molding process, only an abrupt change of directions is possible in general, but that would constitute a considerable burden on the blood.

The object of the present invention is to improve upon a generic filter device so that the transfer of blood from the inlet into the fibers is accomplished at a low load and the fibers are loaded uniformly.

SUMMARY OF THE INVENTION

This object is achieved according to the present invention by a filter device whose membrane is designed in the form of a hollow fiber bundle, its fiber cavities forming a first flow space, with at least one inflow or outflow chamber which communicates with the first flow space being provided for supplying a medium to the hollow fiber bundle or removing a medium from it, said chamber being adjacent to an essentially circular or semicircular channel which communicates with an inlet or outlet of the filter device and is designed to be open in the direction of the ends of the hollow fibers, said channel being arranged approximately centrally with the hollow fiber bundle, having a cross-sectional area that decreases in the direction of flow and having an outside diameter smaller than the diameter of the hollow fiber bundle. This yields, first, the advantage that the blood flow undergoes only relatively gentle and low-stress changes in direction and velocity of flow. With the device according to the present invention, the flow velocity in the path through the essentially circular or semicircular channel gradually approaches the value of the velocity inside the fibers with the device according to the present invention.

Second, this yields the advantage that the blood is distributed in a pattern having approximate radial symmetry due to the changing cross-sectional area along the path through the channel. This means that approximately the same amount of blood flow leaves the channel and flows outward radially in each angular area. This yields a uniform utilization of the individual fibers of the hollow fiber bundle and thus yields optimum utilization of fiber capacity.

In contrast with the previously known solutions to this problem, there is no marked turbulence with the arrangement according to the present invention, but instead the distribution of the fluid or the blood has a mainly uniform radial symmetry.

It is especially advantageous if the end areas of the hollow fibers are held in a casting compound which extends parallel to the channel. The casting compound is usually designed in the form of disks, with the ends of the hollow fibers being arranged in a uniform distribution in the casting compound.

According to a preferred embodiment of the present invention, the height and/or width of the channel decreases in the direction of flow. It is especially advantageous if the cross-sectional area of the channel decreases linearly with the flow path. Such a design yields the result that identical quantities of liquid or blood are discharged from the channel per angle area, thus resulting in a distribution that has approximate radial symmetry.

It is especially advantageous if there is an inlet or outlet extending radially, developing into the channel according to the present invention in its one end area and forming the mouth of a connection of the filter device in its other end area.

The diameter of the circular or semicircular channel may advantageously be 2 to 4 times, preferably 2.5 to 3.5 times, the diameter of the inlet or outlet.

In another embodiment of the present invention, the diameter of the circular or semicircular channel may be less than $9/16$, preferably less than $3/8$, of the diameter of the hollow fiber bundle.

It is especially advantageous if the channel is circular, i.e., circumferential. Thus, not only a semicircular design of the channel is conceivable, but also a complete circulation.

In another embodiment of the present invention, guide elements are provided in the areas adjacent to the essentially circular or semicircular channel, so that the direction of flow of the fluid leaving the channel can be influenced by these guide elements.

The guide elements may be designed as curved ribs. This makes it possible to distribute the fluid, in particular the blood, uniformly and in a defined manner. This may lead to the development of a small central vortex, but it always has radial symmetry.

It is especially advantageous if the ribs are equidistant in the circumferential direction of the channel. In addition, any other desired arrangement of ribs and guide elements is also conceivable.

The hollow fiber bundle may be held in a tubular casing, with a second flow space being formed through the interior of the casing surrounding the hollow fiber bundle, and with the inflow or outflow chamber being arranged in an end cap connected to the casing at the end. End caps may be provided in both end areas of the casing.

According to a preferred embodiment of the present invention, the hollow fiber bundle extends over the entire cross-sectional area of the casing. It is also conceivable for only partial areas of the cross-sectional area of the casing or the casting compound to be provided with hollow fibers.

It is especially advantageous if each of the end caps has two connections, one of which is connected to the first flow space and the other to the second flow space. Thus, an inlet and an outlet are created for each of the flow spaces, which permits continuous flow through both flow spaces accordingly. The assignment as an inlet or outlet is not fixed, because the connections can be exchanged as needed.

In another embodiment of the present invention, the connections are arranged radially. This applies accordingly for the blood side as well as for the connection for the dialysis solution, which is usually carried through the second flow space. The radial arrangement of the connections may have hydrodynamic advantages. In addition, the arrangement of the connections may also be predetermined by the tube system to be used or by the mounting of the filter device.

According to a preferred embodiment of the present invention, the center lines of the connections run parallel to one another. It is also possible for the center lines of the connections not to pass through the mid point of the end cap.

The mouths of the connections may lie in one plane or in parallel planes. The corresponding design depends essentially on the mount holding the filter device, which should permit rapid and reliable replacement of the filter devices. In another embodiment of the present invention, the connections point in opposite directions.

It is especially advantageous if the casing and the end caps are designed as injection molded parts. This guarantees a reliably simple manufacture, with numerous different embodiments being conceivable.

The present invention also concerns an end cap for a filter device according to the present invention having an inflow or outflow chamber adjacent to an essentially circular or semicircular channel, which is designed to be open in the direction of the ends of the hollow fibers of a hollow fiber bundle arranged in a filter device casing that can be connected to the end cap, and being connected to an inlet or outlet of the end cap, arranged approximately centrically to the hollow fiber bundle and having a cross-sectional area that decreases in the direction of flow, and which has an outside diameter which is less than the inside diameter of the area of the end cap accommodating the hollow fiber bundle.

Advantageous embodiments of the end cap are presented by the embodiments according to the claims.

Additional details and advantages of the present invention are explained in greater detail below on the basis of one embodiment illustrated in the figures.

DETAILED DESCRIPTION OF THE INVENTION

Figure 1:
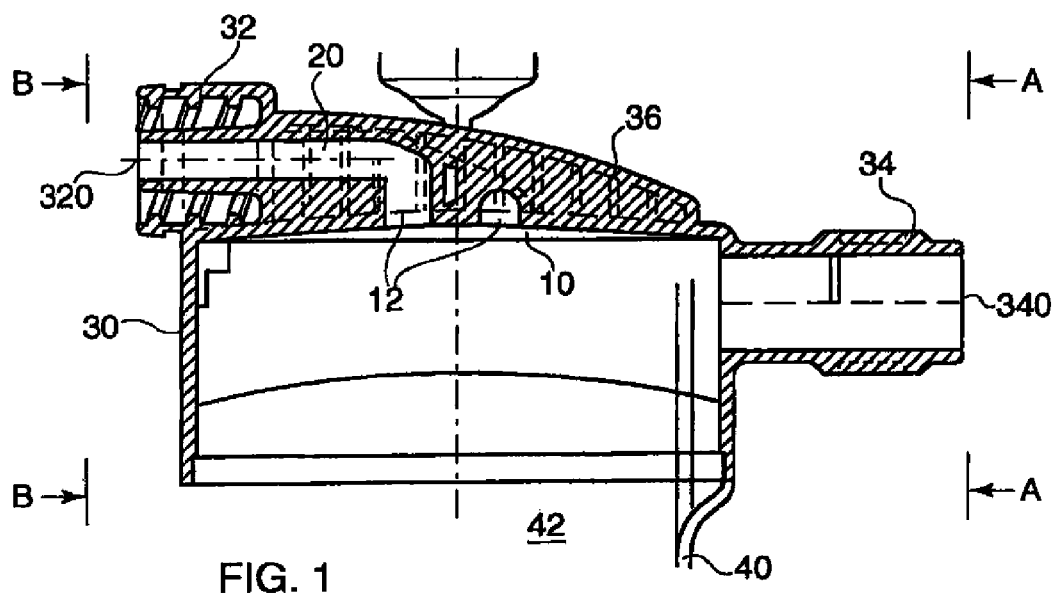
FIG. 1 shows a longitudinal sectional view of an end cap with inflow or outflow chambers having a semicircular channel.

FIG. 1 shows a longitudinal sectional diagram of the end cap 30, which is in fluid-tight connection with the casing 40. End cap 30 has inflow or outflow chamber 10 adjacent to the semicircular channel 12. Liquid leaving semicircular channel 12 is carried into the inflow or outflow chamber 10 and is distributed in an essentially radially symmetrical pattern over the ends of the hollow fibers of a hollow fiber bundle.

Channel 12 is connected to the inlet or outlet 20 which in its end area forms the mouth 320 of connection 32 of the filter device according to the present invention.

End cap 30 is provided with bead 36 which extends radially, with connection 32 being formed in its end area.

In the area of end cap 30 shown at the right in FIG. 1, connection 34 is provided, having mouth 340 which is connected to the second flow space formed by the interior 42 of the casing surrounding the fibers.

Figure 2:
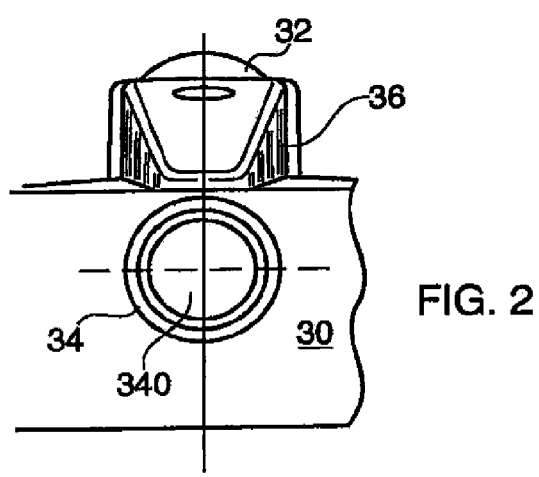
FIG. 2 shows a partial side view of the end cap according to line A-A in FIG. 1.
Figure 3:
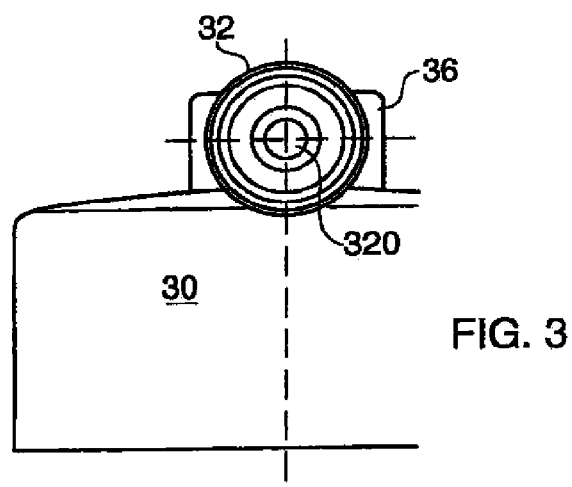
FIG. 3 shows a partial side view of the end cap according to line B-B in FIG. 1.

FIGS. 2 and 3 show the side views of the end cap 30 according to FIG. 1 in the perspectives defined by lines A-A and B-B respectively. Both connection 32 and connection 34 are arranged radially. This is also true of bead 36 in whose end area is arranged connection 32.

Mouths 320 and 340 of connections 32 and 34 lie in parallel planes, but they point in opposite directions, as shown in FIG. 1 in particular. This may be necessary for reasons of compatibility with tubing systems already present or corresponding mounts holding the filters or because of advantages in handling. However, it is essentially also possible to provide the connections on the same side and to arrange the mouths in one plane.

Figure 4:
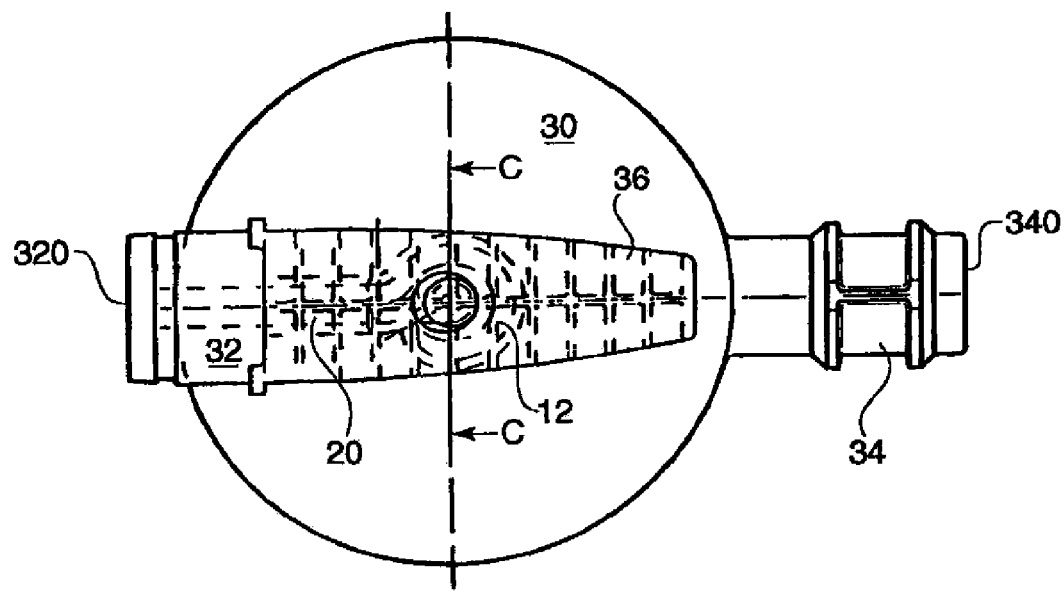
FIG. 4 shows a top view of the end cap according to FIG. 1.

FIG. 4 shows a top view of the end cap 30 and illustrates the arrangement and embodiment of channel 12 and inlet and outlet line 20 with a dotted line.

FIG. 4 shows that the inlet or outlet line 20 running through the connection 32 is arranged radially. Inlet line 20 develops into channel 12, which is semicircular in shape according to this invention and extends approximately centrally through the hollow fiber bundle and/or the casting compound.

The height of channel 12 decreases in the direction of flow, which has the advantage that liquid carried through channel 12 leaves channel 12 in equal distribution over the angular sections, i.e., with radial symmetry, and is carried into the inflow or outflow chamber 10 and is thus distributed uniformly among the fibers of the hollow fiber bundle.

According to the present embodiment, channel 12 is designed so that its height is zero in its end area, i.e., it develops into the bottom of end cap 30.

Figure 5:
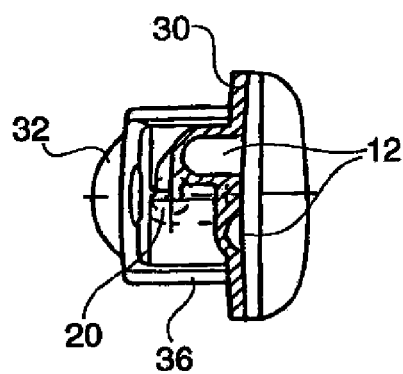
FIG. 5 shows a detailed view of a sectional diagram according to line C-C in FIG. 4.

In a cross-sectional diagram according to line C-C from FIG. 4, FIG. 5 shows the arrangement and the design of channel 12. FIG. 5 shows a cross section of the channel shown at the right in FIG. 5 which is offset with respect to the inlet or outlet 20 because of its semicircular design, and the height of the channel 12 decreases in the direction of flow.

Figure 6:
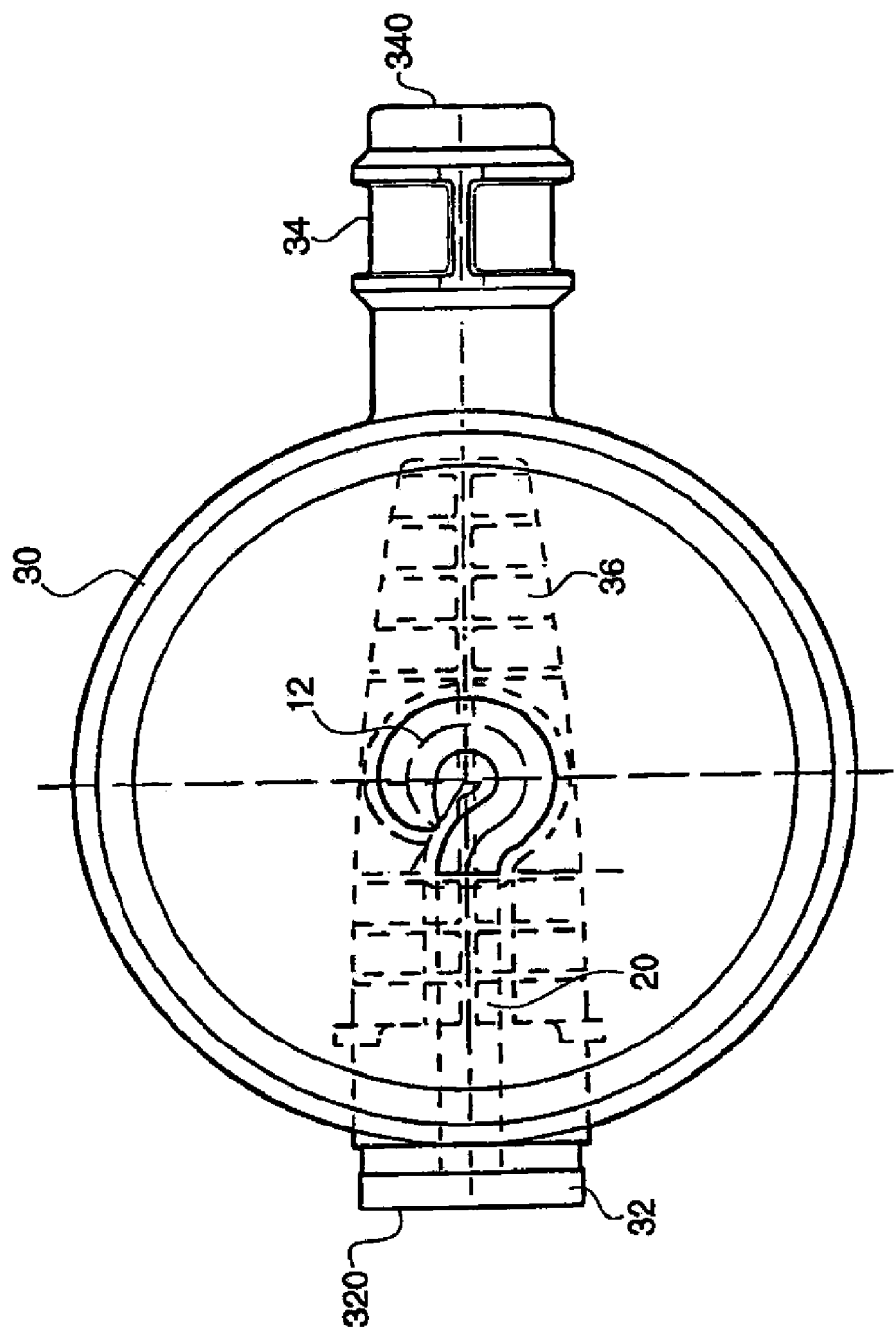
FIG. 6 shows a view of the end cap according to FIG. 1 from beneath.

FIG. 6 shows a bottom view of the end cap 30 according to FIG. 1. FIG. 6 shows a channel 12 having a semicircular shape, and in its outlet end area it develops into the bottom of end cap 30. FIG. 6 also shows that the mid point of the semicircle formed by channel 12 which corresponds to the mid point of the end cap 30 and thus also the mid point of the casting compound or that of the hollow fiber bundle.

Figure 7:
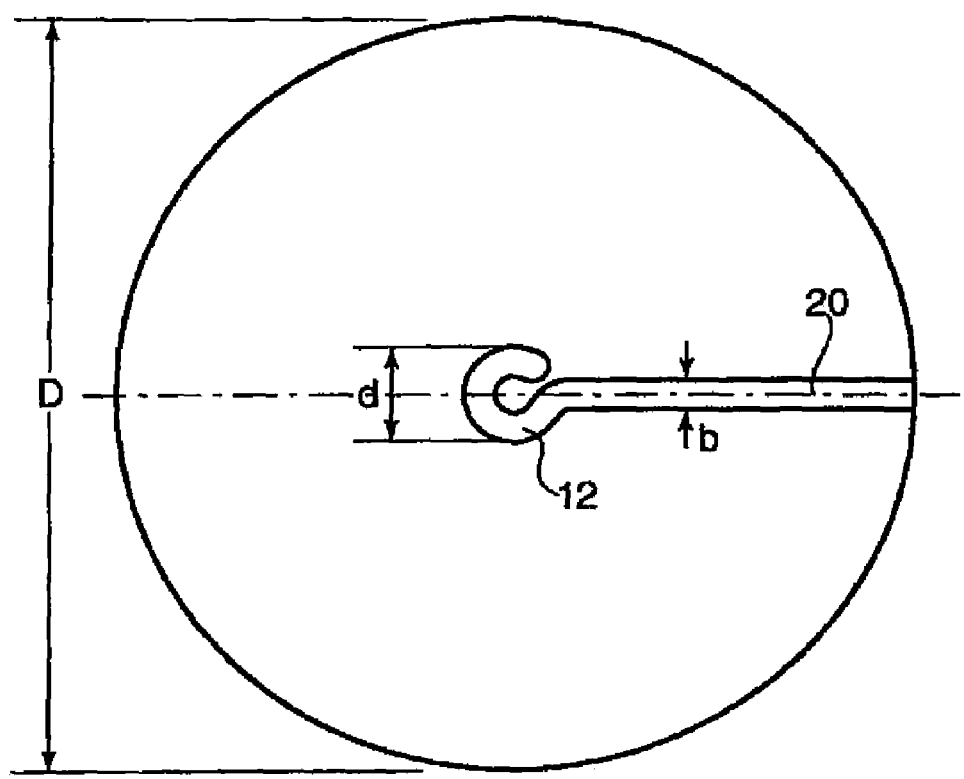
FIG. 7 shows a schematic diagram of the size relationships of the inlet or outlet, the channel and the hollow fiber bundle.

FIG. 7 shows a schematic diagram of exemplary size relationships of the inlet or outlet 20, channel 12, and the hollow fiber bundle characterized by the circle. The diameter (d) of the circular or semicircular channel 12 preferably amounts to 2 to 4 times, more preferably 2.5 to 3.5 times the diameter (b) of the inlet or outlet 20. The diameter (d) of the channel 12 preferably is less than 9/16, more preferably less than 3/8 of the diameter (D) of the hollow fiber bundle.

Figure 8:
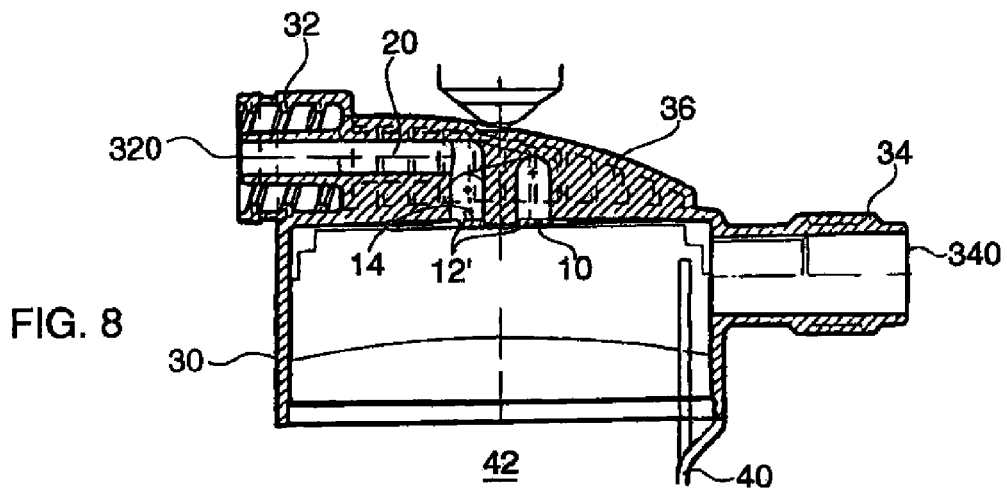
FIG. 8 shows a longitudinal sectional view of an end cap with an inflow or outflow chamber having a circular, i.e., circumferential channel.

FIG. 8 shows a longitudinal sectional diagram of another embodiment of the filter device according to the present invention. The end cap 30 according to FIG. 8 has a circular, i.e., circumferential channel 12'. The cross-sectional area of channel 12' decreases in the direction of flow, which is implemented by the fact that its height decreases in the direction of flow, as shown in FIG. 8.

Curved ribs 14 arranged in the area extending around channel 12' cause the fluid leaving channel 12' to be distributed uniformly into the inflow or outflow chamber 10 or through the hollow fiber bundle in a defined manner. The distance between ribs 14 and the casting compound of the filter is advantageously designed so that almost complete flow control is achieved. This distance is, for example, approximately 0.2 mm. The distance between the casting compound and the connection of end cap 30 inside the circular channel 12' is advantageously somewhat greater, e.g., 0.25 mm.

Figure 9:
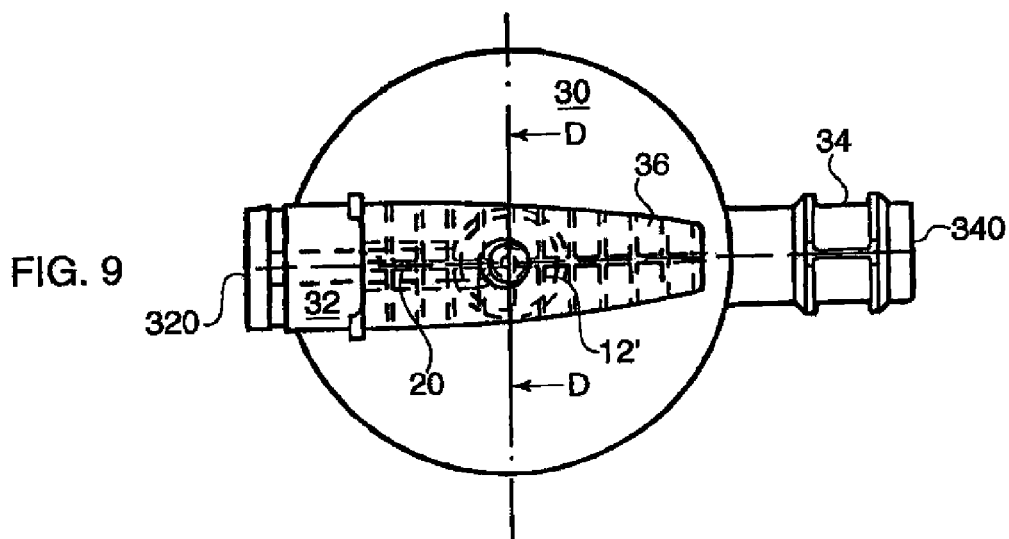
FIG. 9 shows a top view of the end cap according to FIG. 8.

FIG. 9 shows a top view of end cap 30, illustrating that channel 12' in the embodiment according to FIG. 8 is designed to be circular.

Figure 10:
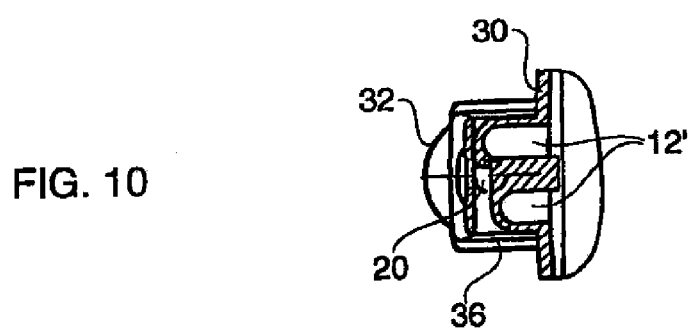
FIG. 10 shows a detailed view of a sectional diagram according to line D-D in FIG. 9.

FIG. 10 shows a cross-sectional diagram according to line D-D in FIG. 9, illustrating an arrangement and design of the channel 12'. A comparison with FIG. 5 shows that the section of the channel shown at the bottom of FIG. 10 has a larger cross-sectional area than in the embodiment shown in FIG. 5, and in each instance the cross-sectional area does not drop back to zero in the remaining course in accordance with the circumferential design of channel 12'.

Figure 11:
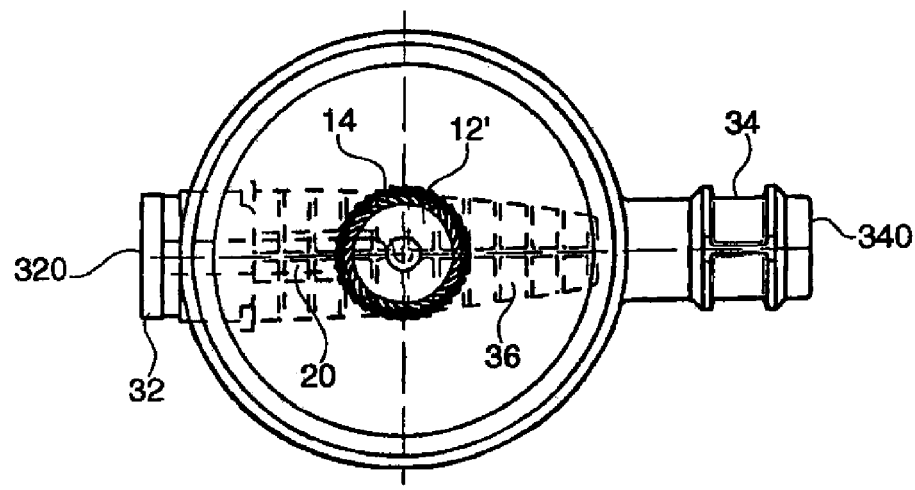
FIG. 11 shows a view of the end cap according to FIG. 8 from beneath.

FIG. 11 shows a bottom view of the end cap in FIG. 8. In this embodiment, channel 12' is designed to be circumferential. Furthermore, it can be seen in this embodiment that ribs 14 are arranged around the circumference of channel 12' and do not run radially outward but instead are arranged with a curvature. Of course, in addition to the embodiment shown here, any other desired arrangement and embodiment of ribs 14 are also conceivable. Ribs 14 serve as guide elements for the liquid leaving the channel 12'. Ribs 14 are approximately one millimeter or a few tenths of a millimeter thick, for example. Due to the design and arrangement of such guide elements, it is possible to distribute the liquid leaving channel 12' in a defined manner and in a defined direction in the inflow or outflow chamber 10 or through the hollow fiber bundle.

Figure 12:
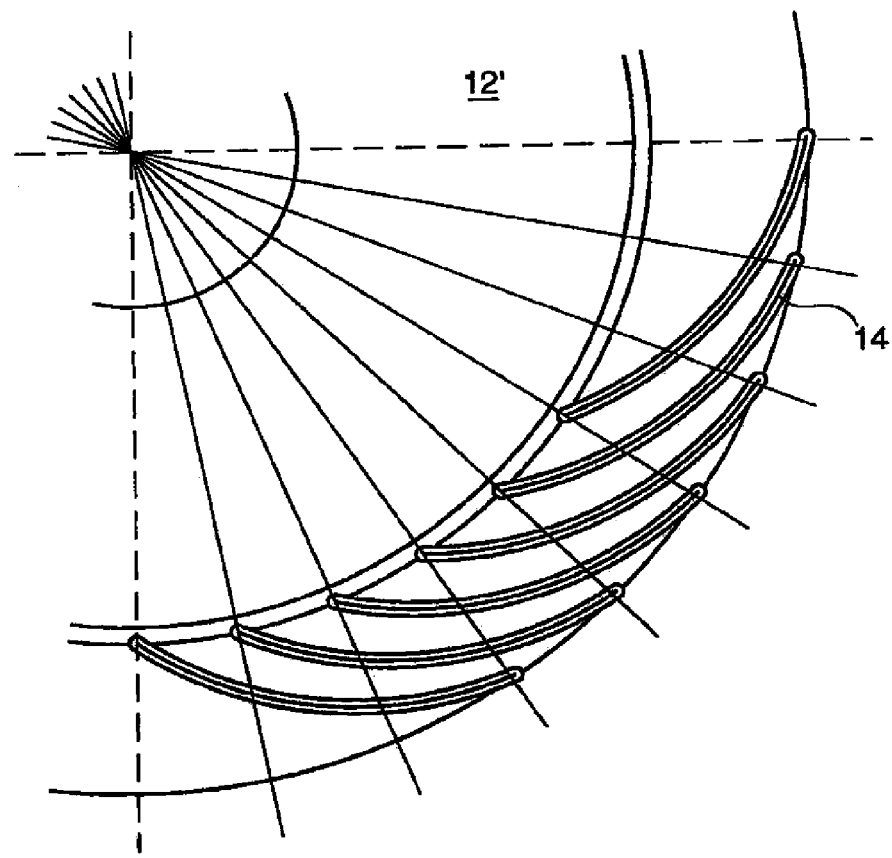
FIG. 12 shows a detailed view of the circular channel and the adjacent guide elements designed as ribs according to FIG. 11.

The arrangement of ribs 14 is shown in the detailed view according to FIG. 12. It can be seen in this embodiment that the ribs 14 are directly adjacent to the channel 12'. Ribs 14 are designed to be equidistant from one another. The distance between the individual ribs decreases in the direction of flow, leading to a corresponding acceleration of the fluid carried through ribs 14.

The arrangement of the guide elements, in particular ribs 14, is conceivable not only with the circumferential design of channel 12' but of course also with a semicircular design according to FIGS. 1 through 7.

Advantageous dimensions of the circumferential channel 12' according to FIGS. 8 through 12 can also be derived from the discussion of FIG. 7 above.

What is claimed is:

1. A filter device comprising:
  a housing;
  a first fluid flow path comprising a hollow fiber bundle contained in the housing;
  a second fluid flow path located between the housing and the first fluid flow path; and
  an end cap attachable to an axial end of the housing, the end cap including
    a fluid chamber in fluid communication with the first fluid flow path;
    a curved channel in fluid communication with the fluid chamber and a first fluid flow path port; and
    a plurality of curved members connected to an upper interior surface of the end cap that is adjacent to the channel, the plurality of curved members forming a plurality of spaces therebetween, the plurality of spaces being axially exposed to the hollow fiber bundle,
  wherein the filter device is a dialyzer.

2. The device of claim 1, wherein the curved channel is selected from the group consisting of circular and semicircular channels.

3. The device of claim 1, wherein the curved channel is arranged approximately in the center of the hollow fiber bundle.

4. The device of claim 1, wherein the first fluid flow path port is an inlet and fluid flows into the inlet, through the curved channel, into the fluid chamber, and into the first fluid flow path.

5. The device of claim 4, wherein cross-sectional area of the curved channel decreases in the direction of fluid flow.

6. The device of claim 4, wherein the cross-sectional area of the curved channel decreases linearly in the direction of fluid flow.

7. The device of claim 4, wherein the height of the curved channel decreases in the direction of fluid flow.

8. The device of claim 4, wherein the width decreases of the curved channel in the direction of fluid flow.

9. The device of claim 2, wherein the outside diameter of the curved channel is smaller than the outside diameter of the hollow fiber bundle.

10. The device of claim 4, wherein fluid flows from the curved channel to the fluid chamber with approximately uniform radial symmetry.

11. The device of claim 1, wherein the ends of the hollow fibers are held in a casting compound, the casting compound extending approximately parallel to the curved channel.

12. The device of claim 1, wherein the fluid port extends radially from the curved channel.

13. The device of claim 1, wherein the diameter of the curved channel is about 2 to about 4 times larger than the diameter of the fluid port.

14. The device of claim 1, wherein the diameter of the channel is about 2.5 to about 3.5 times larger than the diameter of the port.

15. The device of claim 1, wherein the diameter of the channel is less than about 9/16 the diameter of the hollow fiber bundle.

16. The device of claim 1, wherein the diameter of the channel is about 3/8 the diameter of the hollow fiber bundle.

17. The device of claim 1, wherein the curved channel includes guide elements constructed and arranged to influence the direction of fluid flow leaving the channel.

18. The device of claim 17, wherein the guide elements are curved ribs.

19. The device of claim 18, wherein the curved ribs are equidistant from one another circumferentially.

20. The device of claim 11, wherein the hollow fiber bundles extend over substantially over the entire cross-sectional area of the casting material.

21. The device of claim 11, wherein the hollow fiber bundles extend over only a portion of the cross-sectional area of the casting material.

22. The device of claim 1, wherein the end cap further comprises a second fluid flow path port in fluid communication with the second fluid flow path.

23. The device of claim 22, wherein the end cap can be connected to the housing in a fluid-tight manner.

24. The device of claim 22, wherein the first fluid flow path port and the second fluid flow path port are arranged radially on the end cap.

25. The device of claim 22, wherein the center lines of the first fluid flow path port and the second fluid flow path port are parallel to one another.

26. The device of claim 22, wherein the plane of the mouth of the first fluid flow path port and the plane of the mouth of the second fluid flow path port are parallel.

27. The device of claim 22, wherein the mouth of the first fluid flow path port and the mouth of the second fluid flow path port lie in one plane.

28. The device of claim 22, wherein the end cap is a plastic material manufactured by injection molding.

29. The device of claim 22, wherein an end cap is provided at each end of the housing.

30. A filter device comprising:
a) a substantially cylindrical housing;
b) a first fluid flow path comprising a hollow fiber bundle contained in the housing;
c) a second fluid flow path located between the housing and the first fluid flow path;
d) an end cap comprising:
i) a first fluid flow path port;
ii) a fluid chamber in fluid communication with the first fluid flow path; and
iii) a curved channel in fluid communication with the fluid chamber and the first fluid flow path port; and
iv) a plurality of curved members connected to an upper interior surface of the end cap that is adjacent to the channel, the plurality of curved members forming a plurality of spaces therebetween, the plurality of spaces being axially exposed to the hollow fiber bundle,
wherein fluid flows into the first fluid flow path port, into and through the curved channel, into the fluid chamber, and into the first fluid flow path and wherein the filter device is a dialyzer.

31. The device of claim 30, wherein the curved channel is selected from the group consisting of circular and semicircular channels.

32. The device of claim 30, wherein fluid flows from the curved channel into the fluid chamber with approximately uniform radial symmetry.

33. The device of claim 30, wherein an end cap is provided at each end of the housing.

34. An end cap for a filter device comprising:
a) a fluid port;
b) a curved channel in fluid communication with the fluid port;
c) a fluid chamber in fluid communication with the curved channel; and
d) a plurality of radially curved ribs disposed circumferentially around the channel, a distance between circumferentially adjacent curved ribs decreasing in a radially outward flow direction;
wherein the end cap may be connected in fluid tight fashion to a housing containing a fluid flow path comprising a hollow fiber bundle such that fluid flows in the port, into and through the curved channel, into the fluid chamber, and into the fluid flow path.

35. The end cap of claim 34, wherein the curved channel is selected from the group consisting of circular and semicircular channels.

36. The end cap of claim 34, wherein the cross-sectional area of the curved channel decreases in the direction of fluid flow.

37. The end cap of claim 4, wherein the cross-sectional area of the curved channel decreases linearly in the direction of fluid flow.

38. The end cap of claim 34, wherein the outside diameter of the curved channel is smaller than the outside diameter of the hollow fiber bundle.

39. The end cap of claim 34, wherein fluid flows from the curved channel to the fluid chamber with approximately uniform radial symmetry.

40. The end cap of claim 34, wherein the fluid port extends radially from the curved channel.

41. The end cap of claim 34, wherein the diameter of the curved channel is about 2 to about 4 times larger than the diameter of the fluid port.

42. The end cap of claim 34, wherein the diameter of the channel is about 2.5 to about 3.5 times larger than the diameter of the port.

43. The end cap of claim 40, wherein the curved ribs are equidistant from one another circumferentially.

44. The end cap of claim 30, further comprising a second fluid port and wherein the fluid port and the second fluid outlet port are arranged radially on the end cap.

45. The end cap of claim 34, wherein the center lines of the fluid port and the second fluid port are parallel to one another.

46. The end cap of claim 34, wherein the plane of the mouth of the fluid port and the plane of the mouth of the second fluid port are parallel.

47. The end cap of claim 34, wherein the mouth of the fluid port and the mouth of the second fluid port lie in one plane.

48. The end cap of claim 34, wherein the cap is a plastic material manufactured by injection molding.

49. A dialyzer comprising:
   a housing;
   a first fluid flow path comprising a hollow fiber bundle contained in the housing;
   a second fluid flow path located between the housing and the first fluid flow path; and
   an end cap attachable to the casing, the end cap including:
      a fluid chamber in fluid communication with the first fluid flow path;
      a channel in fluid communication with the fluid chamber and a first fluid flow path port; and
      a plurality of curved members connected to an upper interior surface of the end cap that is adjacent to the channel, the plurality of curved members forming a plurality of spaces therebetween, the plurality of spaces being axially exposed to the hollow fiber bundle.

* * * * *

UNITED STATES PATENT AND TRADEMARK OFFICE
CERTIFICATE OF CORRECTION

PATENT NO. : 7,713,412 B2  
APPLICATION NO. : 12/118336  
DATED : May 11, 2010  
INVENTOR(S) : Klaus Heilmann et al.

Page 1 of 1

It is certified that error appears in the above-identified patent and that said Letters Patent is hereby corrected as shown below:

Title Page, Item (73) Assignee please change "GmnH" to --GmbH--

Signed and Sealed this
Seventeenth Day of May, 2011

David J. Kappos
*Director of the United States Patent and Trademark Office*